US005177190A

United States Patent [19]
Rollins et al.

[11] Patent Number: 5,177,190
[45] Date of Patent: Jan. 5, 1993

[54] PURIFIED C5A RECEPTOR FROM HUMAN POLYMORPHONUCLEAR LEUKOCYTES

[75] Inventors: Thomas E. Rollins, North Plainfield; Martin S. Springer, Westfield, both of N.J.

[73] Assignee: Merck & Co., Inc., Rahway, N.J.

[21] Appl. No.: 825,435

[22] Filed: Jan. 22, 1992

Related U.S. Application Data

[63] Continuation of Ser. No. 652,472, Feb. 8, 1991, abandoned, which is a continuation of Ser. No. 447,476, Dec. 18, 1989, abandoned, which is a continuation-in-part of Ser. No. 292,694, Jan. 3, 1989, abandoned.

[51] Int. Cl.$^5$ .................. C07K 15/08; C07K 15/14
[52] U.S. Cl. .................... 530/350; 530/395
[58] Field of Search .................. 530/350, 395, 413

[56] References Cited

U.S. PATENT DOCUMENTS 4,672,044 6/1987 Schreiber.
4,772,584 9/1988 Cleary et al.

OTHER PUBLICATIONS

Matson et al. 1986, LC-GC 4(7): 624–634.
Dialog File 155, Abstract, Occession No. 91378885, Rogers et al. 1991, Biochem J. 278: 405–410.
Dialog File 155, Abstract, Occession No. 91236709 Faussner et al. 1991 J. Biol. Chem. 266(15): 9442–9446.
Hjelmeland et al. 1983 Analytical Biochemistry 130: 485–490.
Wormack et al. 1983, Biochemica et Biophysica Acta 733: 210–215.
Gerard et al., 1988, FASEB J. 2(4) Abstract 2158.
Hjelmeland, L. M. 1980, Proced. Natl. Acad. Sci. 77(11): 6368–6370.
Bio-Rad 1987, Price List M, pp. 84, 85, 91.
Charo et al., 1986, J. Immunol. 136(9): 3412–3419.
Baron and Thompson, Biochemica et Biophisica Acta vol. 382 pp. 276–285 (1975).
Davis, Molecular and Chemical Characterization of Membrane Receptor, pp. 161–178 (1984) vol. 3; Alan Liss Inc. NY, Venter Edition.
Helenius et al., Method in Enzymology, vol. LVI, pp. 734–749 (1979) (1983).
Hjelmeland et al., Anal. Biochem. 130, 72–82 (1983).
Hjelmeland, Proc. Natl. Acad. Sci. vol. 77, No. 11, pp. 6368–6360 (1980).
Rosevear et al., Biochemistry vol. 19, 4108–4115 (1980).
Siciliano et al., J. Biol. Chem. vol. 265 pp. 19568–19574 (1990).
ATCC Catalogue of Cell Lines and Hybridomas, pp. 123 & 139 (1985).
ATCC Catalogue of Cell Lines and Hybridomas, pp. 132 & 154 (1988).
Gerard et al., J. Biological Chem., vol. 264, pp. 1760–1766 (1989).
Gerard, et al., Biochemistry, vol. 29, pp. 9274–9281 (1990).
Webster's Third New International Dictionary (1966) Defining "Approximately".
Huey, R., and Hugli, T. E. (1985) J. Immunol. 135: 2063–2068.
Rollins, T. E., Siciliano, S. and Springer, M. S. (1988) J. Biol. Chem. 260: 520–526.
Mandecki, W. et al. (1986) Gene 43 pp. 131–138.
Chenoweth, D. E., and Hugli, T. E. (1978) Proc. Nat. Acad. Sci. USA 75: 3943–3947.
Rollins, T. E. and Springer, M. S. (1985) J. Biol. Chem. 260: 7157–7160.
Johnson, R. J., Chenoweth, D. E. (1985) J. Biol. Chem. 260: 7161–7164.

Primary Examiner—Robert A. Wax
Assistant Examiner—Keith C. Furman
Attorney, Agent, or Firm—Curtis C. Panzer; Joseph F. DiPrima

[57] ABSTRACT

A method is disclosed for isolating and purifying C5a receptor from human polymorphonuclear leukocytes. C5a is a complement-derived protein which is important as a mediator of inflammatory responses. C5a receptor may be used to screen create and quantify C5a antagonists useful as anti-inflammatory agents and immunoregulants and to generate monoclonal and polyclonal anti-C5a receptor antibodies useful as anti-inflammatory agents and immunoregulants.

6 Claims, 8 Drawing Sheets

SDS - PAGE OF PURIFIED C5a RECEPTOR

PURIFIED C5A RECEPTOR FROM HUMAN POLYMORPHONUCLEAR LEUKOCYTES

This is a continuation of application Ser. No. 07/652,472, filed Feb. 8, 1991, now abandoned, which is a continuation of application Ser. No. 07/447,476, filed Dec. 18, 1989, now abandoned, which is a continuation in part of application Ser. No. 07/292,694, filed Jan. 3, 1989, now abandoned.

This invention relates to a novel purified receptor for the complement-derived protein C5a. The receptor is useful for screening creating and quantifying C5a antagonists and for generating monoclonal and polylclonal anti-C5a receptor antibodies for use as anti-inflammatory agents and immunoregulants.

The importance of C5a receptor finds its origin in its relationship with complement derived C5a and its role in the overall immune response.

The complement system is a complex group of proteins present in body fluids that, working together with antibodies or other factors, plays an important role as mediators of immune, allergic, immunochemical and immunopathological reactions. Activation of the complement system can result in a wide range of reactions such as lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins, when activated, combine with still others to form enzymes that cleave and activate still other proteins in the system. The sequential activation of these proteins follows two main pathways, the classical pathway and the alternative pathway. Both pathways use a common terminal trunk that leads to cell lysis or virus inactivation.

The classical pathway can be activated by antigen-antibody complexes, aggregated immunoglobulins and non-immunological substances such as DNA and trypsin-like enzymes. The classical pathway includes activation of C1, C4, C2 and C3. These components can be grouped into two functional units: C1 or recognition unit; and C4, C2 and C3 or activation unit. Five additional components denominated C5, C6, C7, C8, and C9 define the membrane attack unit forming the terminal trunk common to both pathways.

The 74-residue glycopeptide C5a is cleaved from the amino terminus of C5 when the complement system is activated. C5a has been shown to stimulate contraction of smoothe muscle, enhance vascular permeability, promote the synthesis and release of other mediators including leukotrienes, prostaglandins, platelet-activating factor, and histamine. In vivo, C5a results in the accumulation of polymorphonuclear leukocytes (PMN) and marcrophages at site of inflammation, one of the hallmark events of an acute inflammatory response. In vitro, C5a is a potent chemotaxin for leukocytes, most notably PMN and macrophages, and it activates PMN causing them to release a variety of hydrolytic enzymes and to generate oxygen radicals. These latter phenomena are thought to be responsible not only for the killing of microorganisms but for much of the tissue destruction that takes place in inflammatory situations.

The existence of the C5a receptor of PMN was first demonstrated and its binding properties first described by Chenoweth and Hugli in 1978. See Chenoweth, D. E., and Hugli, T. E. (1978) *Proc. Nat. Acad. Sci. USA* 75: 3943-3947. The binding subunit of the receptor from PMN was first identified and its size estimated in 1985. See Rollins, T. E., and Springer, M. S. (1985) *J. Biol. Chem.* 260: 7157-7160; Johnson, R. J., and Chenoweth, D. E. (1985) *J. Biol. Chem.* 260: 7161-7164; Huey, R., and Hugli, T. E. (1985) *J. Immunol.* 135: 2063-2068. The solubilization of the receptor in an active state was first described by Rollins, Siciliano and Springer in 1988. See Rollins, T. E., Siciliano, S., and Springer, M. S. (1988) *J. Biol. Chem.* 263: 520-526.

While the binding subunit of the C5a receptor has been identified, and the receptor has now been solubilized in an active state, little is known about the mechanism of signal transduction except that it involves one or more GTP binding proteins. Several groups have shown that pertussis toxin blocks C5a mediated cellular activation and that GTP analogs alter the affinity of C5a for its receptor. We have now provided evidence that the receptor exists in at least 2, and probably 3, states whose affinities are determined by interaction with G-proteins. See Sicilliano, S. J., Rollins, T. E., and Springer, M. S. (1988) J. Fed. Amer. Soc. Exp. Biol. 12: A1461. Further, these interactions are preserved following detergent solubilization of the receptor. Our data imply that the receptor is solubilized as a complex with one or more of the G-proteins.

Isolated purified C5a receptor may be used to obtain the sequence data needed for cloning the receptor. For example, purified receptor can be subjected to SDS polyacrylamide gel electrophoresis and then electrophoretically transferred to nitrocellulose paper. The receptor can then be subjected to proteolytic degradation, the peptides isolated and sequenced. Sequence data can be constructed from the DNA probes for cloning the C5a receptor gene.

Isolated purified C5a receptor may be used to find and create a C5a antagonist. First, the isolated receptor can be used to screen individual compounds, mixtures of compounds and natural product broths for entities which inhibit the binding of C5a to the receptor. Secondly, structural studies can be carried out to elucidate the molecule attractions and interactions which are responsible for the binding of C5a to the receptor. These studies may include site directed mutagenesis of the receptor, NMR spectroscopy and x-ray crystallography of the purified receptor, and receptor C5a complexes.

Isolated purified C5a receptor may be used to develop compounds which interfere with the interactions responsible for the binding of C5a to the receptor and thereby inhibit biological responses. It may also be used to verify and evaluate the presence of elevated C5a.

Isolated purified C5a receptor may be used to develop antibodies, both monoclonal and polyclonal, which inhibit bind of C5a to the receptor and thereby inhibit the biological responses thereto. Such antibodies may also inhibit the activity of receptor by other means and thereby also inhibit biological responses.

Finally in addition to binding C5a, the C5a receptor interacts with both a GTP-binding protein and cytoskeletal elements. These interactions are required for signal transduction and therefore the biological responses initiated by the binding of C5a to its receptor. Site directed mutagenesis as well as NMR studies and x-ray crystallography of the isolated purified receptor may be conducted to determine the molecular nature of these interactions.

SUMMARY OF THE INVENTION

The invention encompasses a purified isolate having C5a binding activity and methods of preparing same. In the method, an impure polypeptide preparation is solubilized in a detergent, and a fraction thereof having C5a binding activity is isolated by chromatography over an affinity column.

BRIEF DESCRIPTION OF THE DRAWINGS

FIG. 7 is an SDS-PAGE radiograph showing soluble receptor and membrane-bound receptor each incubated and cross-linked with $^{125}$I-C5a.

DETAILED DESCRIPTION OF THE INVENTION

Figure 1:
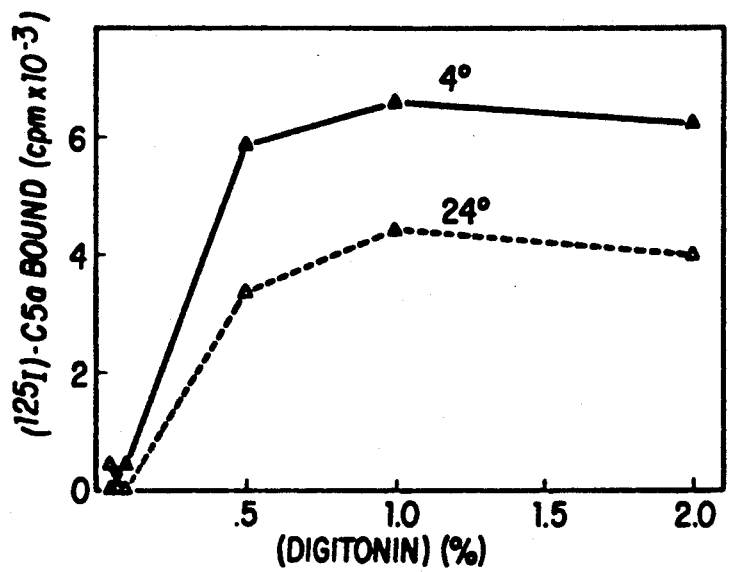
FIG. 1 shows the solubilization of C5a receptor as a function of digitonin concentration.

In a first embodiment the invention encompasses a method of isolating a purified polypeptide having C5a binding activity comprising the steps of:

(a) solubilizing an impure preparation having C5a binding activity;

(b) contacting the impure preparation with a matrix to which an agent specific for C5a binding activity has been bound;

(c) adsorbing from the impure preparation, polypeptide having C5a binding activity onto said matrix;

(d) removing the impurities from the polypeptide bound to said agent;

(e) desorbing the polypeptide from said matrix; and (f) recovering the highly purified and concentrated polypeptide.

The impure preparation of choice is Human PMN isolated from a leukocyte concentrate. Macrophage, eosinophil, ATCC U937 and HL60 (transformed cell lines) preparations may also be used.

In a second embodiment, the invention also encompasses the product of the above method of preparation.

In a third embodiment the invention also encompasses a highly purified and concentrated polypeptide having C5a binding activity.

In one class of the third embodiment the invention encompasses a C5a receptor preparation, the preparation having a C5a binding activity substantially equal to that of intact C5a receptor and being substantially free of cellular matter and plasma with the proviso that the preparation need not be substantially free of one or more associated G-proteins.

To prepare membranes, human PMN are isolated from leukocyte concentrates on a gradient such as Ficoll-Hypaque gradient (English, D., and Andersen, B. R. (1974) *J. Immunol. Methods* 5: 249–255) followed, where applicable, by an ammonium chloride or similar step to lyse red blood cells. The cell preparation can then be resuspended at $10^5$ to $10^7$/ml in a Hanks' or similar balanced salt solution. We found a salt solution comprising Hanks' containing 2.5 mM $MgCl_2$, 0.1% gelatin, 100 units/ml DNase I, 0.1 mM PMSF to be satisfactory.

To ensure against protein degradation, a protein inhibitor cocktail such as that containing 10 $\mu$g/ml each of aprotinin, chymostatin and leupeptin and 10 $\mu$g/ml of phenylmethylsulfonyl fluoride (PMSF) is added to the solution. However, as appreciated by those skilled in the art, the inhibitor cocktail may oftentimes be omitted without discernable detrimental effect.

The suspension should then be fully mixed and then equilibrated at 100 to 400 p.s.i. for 10–20 minutes in a nitrogen bomb. After equilibration, the pressure is returned to one atmosphere, and the contents evacuated into one volume of 0.5M $KHCO_3$ containing 25 mM EDTA and the above protease inhibitor cocktail. The material is then centrifuged at conditions suitable for remand of PMN membranes or other fraction having C5a receptor activity, such as can accomplished at $400 \times g$ for 10 min, $10^4 \times g$ for 20 min, and $10^5 \times g$ for 45 min at 4° C. The final pellet is then resuspended in approximately 10 mM HEPES, pH 6–8, containing above protease inhibitor cocktail. The resuspended pellet is then homogenized.

The PMN membranes or other impure preparation having C5a receptor activity is solubilized in a suitable buffer such as HEPES or TRIS (pH 6–8), containing the above inhibitor cocktail and approximately 0.5 to 2.0% of a suitable detergent, such as digitonin or $\beta$-dodecylmaltoside, CHAPS, deoxycholate, octylglucopyranoside, or NONIDET. (Note that CHAPS is (3[(3-cholamidopropyl)-dimethylammonio-2-hydroxy-1-propanesulfonated); NONIDET P-40 is an octylphenol-ethylene oxide condensate containing an average of 9 moles ethylene oxide per mole of phenol. These detergents are available from the Sigma Chemical Company, Box 14508, St. Louis MO 63178 P-40. Typically we use 1% digitonin in 50 mM HEPES. (Rollins, T. E., Siciliano, S., and Springer, M. S. (1988) J. Biol. Chem. 260: 520–526 provides a more complete type description of our work concerning the selection of detergent.) The detergent/protein ratio is preferably 10/1 (g/g) or greater. Particulates are then removed by Centrifugation. Suitable conditions for centrifugation have been found to include $225,000 \times g$ in a BECKMAN TL100.2 rotor for 7 minutes, or alternatively $160,000 \times g$ for 3 minutes at 22° C. in a BECKMAN.

The supernatant containing the fraction having C5a receptor activity is incubated for from 15 min to 24 hours at 4°-20° C. with an AFFI-GEL 10 and AFFI-GEL 15 [BIO-RAD Laboratories] matrix to which C5a has been linked. AFFI-GEL 10 is an N-hydroxysuccinimide ester of a derivatized crosslinked agarose gel bead containing a neutral 10-atom spacer arm. Affi-Gel ®15 differs from Affi-Gel ® 10 in that the spacer arm is 15 atoms long and contains a cationic charge. The matrix is then poured into a small column and sequentially washed with 50 mM HEPES, pH 6-8, containing 0.05 to 0.5% detergent and protease inhibitor cocktail, and then 50 mM HEPES, pH 6-8, containing approximately 0.05-0.5% detergent (as enumerated above), approximately 0.3 to 0.5M NaCl and protease inhibitor cocktail. The receptor is eluted with a pH 4.0 to 5.0 buffer, such as formic acid containing 0.05 to 0.5% detergent, approximately 0.2M of a suitable chaotrope such as KSCN, $HClO_4$ or NaI, and the protease inhibitor cocktail.

The fractions containing the C5a receptor activity are pooled, concentrated, and then chromatographed. Satisfactory results have been achieved with concentration on an AMICON CENTRICON 30 concentrator followed by gel filtration chromatography over two serially linked TSK 4000sw columns (1×60 cm) in 0.1M HEPES, pH 7.2, containing 0.05% suitable detergent (as enumerated above). Note that the AMICON CENTRICON 30 is an ultrafiltration membrane with a nominal cutoff of 30,000 molecular weight. The TSK 4000sw is a gel column useful for aqueous solvents which contains a porous gel which is rigid, hydrophilic, and shperical with particles of 10 to 30 μm diameter. The active fractions are pooled and concentrated.

Further purification may be achieved through subsequent ion-exchange chromatography. MONO Q FPLC columns at approximately 1 ml per minute with a linear solvent gradient (30 minutes; solvent A=20 mM TRIS, pH 7.5 and solvent B=20 mM TRIS+0.5 m NCl) has proven satisfactory. Note that the MONO Q FPLC column is a product of Pharmacia and is an ion exchange column suitable for use at up to 1500 psi.

A variety of alternative detergents was surveyed for their ability to solubilize the C5a receptor from PMN membranes in a state which still allowed the molecule to bind C5a. As can be seen in Table 1, the most effective of these agents were digitonin and β-dodecyl maltoside. Smaller but still significant amounts of solubilization were also achieved with deoxycholate and the zwitterionic detergent CHAPS.

TABLE I

Solubilization of The C5a Receptor With Various Detergents

| Detergent | $^{125}$I-C5a bound cpm |
|---|---|
| CHAPS | 900 |
| Deoxycholate | 1,000 |
| Digitonin | 4,900 |
| β-Dodecyl maltoside | 2,900 |
| NONIDET P-40 | 200 |
| Octyl glucoside | 0 |
| TX-114 | 0 |
| Buffer | 0 |

In the survey, approximately 5 μg of membrane protein was treated with the listed detergents, at final concentrations of 1%, for 60 minutes at 4° C. The samples were centrifuged at 160,000×g and the supernatants were tested for binding activity as described below The values listed in Table I have had nonspecific binding backgrounds substracted (on average 1,000 cpm). Note that TX-114 is a product of Rohm & Haas an is a polyoxyethylene ether useful as a non-ionic detergent.

In additional experiments (results not shown) the ability of digitonin and β-dodecyl maltoside to release binding sites from the membrane was determined by comparing the total binding activity of the extracts, at saturation, with that of an equivalent amount of intact membrane. In the two experiments in which a direct comparison was made the efficiencies of the detergents appeared to be similar, both solubilized 30-35% of the receptors initially present in the membrane. However, over the course of the work we did observe variability from experiment to experiment and it is our impression that, on average, digitonin was more efficient than β-dodecyl maltoside (for an example, see Table I).

The dependence of the solubilization of receptor on the concentration of digitonin at temperatures of 4° and 24° C. is shown in FIG. 1. Approximately 5 μg of membranes was treated with the indicated concentrations of digitonin for 30 min at 4° C. (▲) and 24° C. (Δ). The 160,000×g supernatants were tested for their ability to bind $^{125}$I-C5a as described in the procedure section.

Above 0.5% detergent, the curves are shallow with a broad optimum for release of receptor centered at about 1%. The greater yield of receptor observed at 4° C., as compared with 24° C., is due to the instability of the receptor at 24° C. and not to a difference in solubilization per se (data not shown). Solubilization reached its maximum level within 30 minutes and was not increased with incubations as long as 24 hours (data not shown). Similar results procedures were also obtained with β-dodecyl maltoside.

The following procedures were used to identify and evaluate products circumscribed by the present invention.

Binding Assays-All assays, except where noted, were performed at 4° C., with freshly thawed membranes or freshly prepared soluble receptor. To assay intact membranes, assay buffer (50 mM HEPES, pH 7.2, containing 1 mM $CaCl_2$, 5 mM $MgCl_2$, 0.1 mM PMSF, 0.1% bacitracin, and 0.5% bovine serum albumin), $^{125}$I-C5a (typically 0.1 ng), and membrane (typically 0.5 μg) were added sequentially to a final volume of 200 μl. After incubation for 60-90 minutes 2 ml of assay buffer was added, the solution mixed, and the sample filtered through either a WHATMAN GF/C filter treated with 0.33% polyethyleneimine or an untreated MILLIPORE GVWP filter. See (Bruns, R. F., Lawson-Wending, K., and Pugsley, T. A. (1983) Anal. Biochem. 132, 74–79). The filters were then counted in a Packard 460 γ-counter. Note that WHATMAN GF/C is a glass fiber filter having a nominal pore size of 1.2 μm; and MILLIPORE GVWP is a microfiltration membrane of polyvinylidene difluoride having a pore size of 0.22 μm. Nonspecific backgrounds were determined by including 20 ng or more of unlabled C5a in the incubation mixture. To assay soluble receptor, assay buffer, solubilized membrane (typically 5 μl) and $^{125}$I-C5a were mixed to a final volume of 200 μl and incubated for 15-30 minutes, at which time 500 μl of 0.1% bovine γ-globulin and 500 μl of 30% polyethylene glycol were added sequentially with vigorous mixing. After an additional 5 minutes, the sample was filtered and washed with 2 ml of a 9% PEG solution. (Precipitation is essentially complete in less than one minute and the precipitated receptorligand complex is stable for more than 30 minutes.)

For purposes of this specification a preparation or isolate having a C5a binding of greater than two times the non-specific binding activity of the test sample is said to have C5a receptor activity.

Purification of C5a from Plasma and Iodination of C5a—Frozen plasma was thawed, made 1 mM in the carboxypeptidase inhibitor (Hugli, T. E., Gerard, C., Kawahara, M., Schaetz, M. E., II, Barton, R., Briggs, S., Kippel, G., and Russell, S. (1981) Mol. Cell. Biochem. 41, 59–66), and then centrifuged at $10^4 \times g$ to remove residual cells. Fleischman's active dry yeast was boiled in water (10 g/100 ml) for 30 minutes and then added to the plasma at a final concentration of 6 mg/ml. The yeast-treated plasma was activated by incubation at 37° C. for 40 minutes and the material then heated at 56° C. for 60 minutes. Solids were removed by centrifugation at $10^4 \times g$ for 10 mins. The protease inhibitors aprotinin, chymostatin, and leupeptin, 10 μg/ml each, and PMSF, 10 μM, as well as EDTA, 0.1 mM, were added and maintained at these concentrations through the Bio-Gel P-60 step. The material was then passed over an affinity column made by coupling rabbit anti-human C5a to AFFI-GEL ®10 (20 mg of IgG/ml of resin). The absorbed material was eluted with 1M acetic acid, and the eluate was neutralized with ammonium hydroxide. The eluate was concentrated using an AMICON YM-5 membrane and the purification completed by chromatography over BIO-GEL P-60 and PHARMACIA MONO S. Note that AMICON YM-5 membrane is a hydrophilic ultrafiltration membrane with low non-specific protein binding having a nominal molecular weight cuttoff of 5000; BIO-GEL P-60 is a product of Bio-Rad and is a polyacrylamide having a fraction range of 3,000 to 60,000 Daltons; PHARMACIA MONO S is a strong cation exchanger based on a beaded hydrophilic resin. It has a particle size of 10 μm and possesses $-CH_2-SO_3^-$ as the charged group. columns. Iodination was carried out with the use of chloramine T. (Rollins, T. E., and Springer, M. S. (1985) J. Biol. Chem. 260, 7157-7160). The $^{125}I(-C5a)$ (100–200 μCi/μg) produced by this procedure had the same affinity for the receptor as did the nonderivatized protein. Concentrations of C5a were determined by amino acid analysis and by RIA (Amersham Corp.).

Cross-linking—The procedure to identify the receptor on intact membranes was the same as that for the binding assay through the incubation step (30 μg of membrane, 0.6 ng of $^{125}I$-C5a). At this point the membranes were pelleted, washed once, and resuspended in 50 mM HEPES buffer, pH 8.0, containing 0.1 mM PMSF. The cross-linking agent ethylene glycolbis(succinimidylsuccinate) (250 μM) was added and the mixture incubated for 30 min, at which time the reaction was quenched with an excess of Tris-Cl. SDS-PAGE was then performed. To cross-link C5a to the β-dodecyl maltoside-solubilized receptor, $^{125}I$-C5a (0.8 ng) was bound to the solubilized membrane (125 μg) as described above followed by the addition of 250 μM EGS. After 30 min, the reaction was quenched with Tris-Cl. An equal volume of boiling Laemmli sample buffer, containing 1% 2-mercaptoethanol, was added and the mixture boiled for 5 min. The sample was then concentrated using an Amicon Centricon 30 filter unit and subjected to SDS-PAGE. This concentration procedure was employed to limit the amount of β-dodecyl maltoside present during electrophoresis because this detergent interfered with SDS-PAGE, causing extreme lane spreading and band distortion.

SDS-gel Electrophoresis of Products—The SDS-Page electrophoresis was carried out under reducing conditions in polyacrylamide gels according to the method of Laemmli. See: Laemmli, U.K. (1970) Nature 227, 680–685; Rollins, T. E., and Springer, M. S. (1985) J. Biol. Chem. 260, 7157-7160. According to the procedure, gels containing 4 percent (stacking gel), 8.0 percent or 10 percent acrylamide were prepared from a stock solution of 30 percent by weight of acrylamide and 0.8 percent by weight of N,N'-bis-methylene acrylamide. The final concentrations in the separation gel were as follows: 0.375 M Tris-HCl (pH 8.8) and 0.1 percent SDS. The gels were polymerized chemically by the addition of 0.025 percent by volume of tetramethylethylenediamine (TEMED) and ammonium persulphate. $10 \times 15$ cm gels were prepared in glass plates with an inside width of 1.5 mm. The stacking gels of 4 percent acrylamide and a length of 4 cm contained 0.125M Tris-HCl (pH 6-8) and 0.1 percent SDS and were polymerized chemically in the same way as for the separating gel. The electrode buffer (pH 8.3) contained 0.025M Tris and 0.192M glycine and 0.1 percent SDS. The samples (0.2–0.3 ml.) contained the final concentrations ("final sample buffer"): 0.0625M Tris-HCl (pH 6.8), 2 percent SDS, 10 percent glycerol, 5 percent 2-mercaptoethanol and 0.001 percent bromophenol blue as the dye. The proteins were completely dissociated by immersing the samples for 5 minutes in boiling water. Electrophoresis was carried out with a current of 3–20 mA per gel until the bromophenol blue marker reached the bottom of the gel. The proteins were fixed in the gel with 10 per cent trichloroacetic acid (TCA) for 30 minutes then stored in 50% methanol overnight. The gels were then stained using silver nitrate and photographed.

The following procedures may be followed for preparation of the requisit immobilized C5a. Recombinant procedures such as that described below are generally advantageous where large quantities of C5a are desired.

Purified C5a from Human Plasma—The Procedure used was derived from that of Fernandez and Hugli (Fernandez, H. N., and Hugli, T. E. (1976) J. Immunol. 117, 1688–1694). Fresh plasma, made 1 mM in the carboxy peptidase inhibitor, as first described by Hugli et al. (Hugli, T. E., Gerard, C., Kawahara, M., Schaetz, M. E., II, Barton, R. Briggs, S., Koppel, G., and Russell, S. (1981) Mol. Cell. Biochem. 41, 59–66), was centrifuged at $5,000 \times g$ to remove residual cells. Active dry yeast that had been boiled in water (10 g/100 ml) for 30 minutes was added to the plasma and the mixture was incubated for 30 minutes at 37° C. followed by centrifugation at $4,000 \times g$ for 15 minutes. The superantant was collected, made 1N in HCl and kept at room temperature for 20 minutes. After centrifugation at $10,000 \times g$ for 15 minutes, the superantant was collected and dialyzed against $H_2O$. The dialysate was lyophilized and stored at $-70°$ C. until it was convenient to continue purification. The lyophilizate was dissolved in 25 mM phosphate buffer, pH 7, containing 0.1 mM carboxypeptidase inhibitor and EDTA at the listed concentrations. After 45 minutes the mixture was placed on ice and centrifuged at $18,000 \times g$ for 30 minutes at 4° C. The supernatant was collected and centrifuged at $50,000 \times g$ for 30 minutes at 4° C. This supernatant was pumped directly onto a SP-SEPHADEX C-25 column ($5 \times 90$ cm). The column was washed with two column volumes of 25 mM phosphate buffer, pH 7.0, and developed with a linear gradient of 0.0 to 0.6M NaCl. The active fractions were pooled and concentrated using an AMICON YM5 membrane. The concentrate was then chromatographed over a BIO-GEL P-60 column (5×100 cm) in 0.1M ammonium formate, pH 5.0. The active fractions were pooled, lyophilized, and redissolved in the same formate buffer. This material was chromatographed over a 0.9×25-cm VYDAC $C_4$ reverse-phase column (214TP510) using a 22.5–50% gradient of acetonitrile in 0.1% trifluoroacetic acid over 60 ml at a flow rate of 1 ml/minute. Note that the 214TP510 is a reverse phase C-4 HPLC separation material, particle size 10 u. The fractions were dried, resuspended in 0.1M ammonium formate, and tested for activity. The active fraction were pooled chromatographed on a PHARMACIA Mono-S column using a 0.1–0.5M gradient of ammmonium bicarbonate, pH 8.5, over 35 ml at a flow rate of 1 ml/minute. The active fractions were dried, redissolved in ammonium formate, ph 5, without inhibitors and stored at −70° C. Concentrations were determined both by amino acid analysis and the commercially available C5a radioimmunoassay kit (Upjohn). All dilutions of the stock C5a were made in 50 mM HEPES, pH 7.5, containing 1 mM $CaCl_2$, 5 mM $MgCl_2$, and 0.5% bovine serum albumin. We find that dilution into other buffers causes a loss of C5a.

Recombinant C5a

Where large quantities of C5a are required, it may be desirable to use a recombinant product. Because of the availability of a recombinant product, in house, we use recombinant human C5a product expressed in IHa68 yeast. While this particular expression system is not widely available to the public, the human C5a sequence is generally known and an *E. coli* expression system for it has been published (Mandecki, W., et. al. High-level expression of a gene encoding the human complement factor C5a in Escherichia coli *Gene* 43 (1986) p 131-138).

Immobilization of C5a—Affi-Gel ® 10 resin is transferred in an isopropyl alcohol slurry to a glass fritted funnel column. The solvent is then drained. The column is then washed with 3 bed volumes of water at 4° C. and the slurry transferred to a 17×100 mm test tube. A solution comprising 26 mg rC5a (dissolved in 4.0 ml 50 mM HEPES pH 7.7), 10 µl $^{125}$I-C5a (as tracer), $1.63 \times 10^{-6}$ Moles glycine and sufficient 0.1M HEPES pM 7.5 made up to 7.8 ml, is then added to the tube. The components are allowed to react for 4 hours at 4° C. with continuous mixing. The product solution is then spun at 1000×g for 5 minutes at 4° C. The supernatant is then counted in γ-counter (to identify presence of tracer.) 100 µl of 1.0 m glycine are added to quench reaction. The reaction is considered to be quenched after 60 minutes at 4° C. with continuous mixing. The resin is then washed according to the following protocol:
A. 0.1M Na acetate, pH 4.5
B. 0.1M HEPES, pH 7.2, 1.0M NaCl
C. 0.1M HEPES, pH 7.2.
The resulting resin linked C5a may be stored in 0.1M HEPES, pH 7.2 with $10^{-4}$M PMSF, and the protease inhibitor cocktail.

The following Examples are included to illustrate the methods and products of Applicants invention and are not to be considered as limiting the invention as set forth in the claims appended thereto.

EXAMPLE 1

Human PMN were isolated from leukocyte concentrates on a Ficoll-Hypaque gradient (English, D., and Andersen, B. R. (1974) *J. Immunol. Methods* 5: 249-255) followed by an ammonium chloride step to lyse red blood cells. The PMN were then resuspended at $10^7$/ml in Hanks' balanced salt solution containing 2.5 mM $MgCl_2$, 0.1% gelatin, 100 units/ml DNase I, 0.1 mM PMSF and the protease inhibitor cocktail and then equilibrated at 400 p.s.i. for 20 min in a nitrogen bomb. The bomb was then quickly evacuated into 1 volume of 0.5M $KHCO_3$ containing 25 mM EDTA and the protease inhibitors at the above concentrations. The material was centrifuged at 400×g for 10 min, $10^4$×g for 20 min, and $10^5$×g for 45 min at 4° C. The final pellet was resuspended in 10 mM HEPES, pH 7.2, containing the protease inhibitor cocktail. The resuspended pellet is the homogenized at 20 strokes in a glass homogenizer.

Solubilization of C5a Receptor

The membranes were solubilized in 50 mM HEPES, pH 7.2 containing 1% digitonin and the protease inhibitor cocktail at 4° C. and then centrifuged at 225,000×g in a Beckman ® TL100.2 rotor for 7 min to remove particulates.

Isolation and Purification of Solubilized C5a receptor

The supernatant was incubated for 60 min at 4° C. with an AFFI-GEL 10 matrix to which C5a had been linked as described supra.

The matrix was then poured into a small column and sequentially washed with 50 mM HEPES, pH 7.2, containing 0.05% digitonin and the protease inhibitor cocktail, and then 50 mM HEPES, pH 7.2, containing 0.5% digitonin, 0.5M NaCl and the protease inhibitor cocktail. The receptor was eluted with 50 mM formic acid, pH 4.0, containing 0.05% digitonin, 0.2M KSCN, and the protease inhibitor cocktail. The fractions containing the active receptor were pooled, concentrated on an Amicon ® Centricon 30 concentrator and then chromatographed over two serially linked TSK 4000sw columns (1×60 cm) in 0.1M HEPES, pH 7.2, containing 0.05% diginition.

Properties of Products Having C5a Receptor Activity Solubilized C5a Receptor

Figure 2:
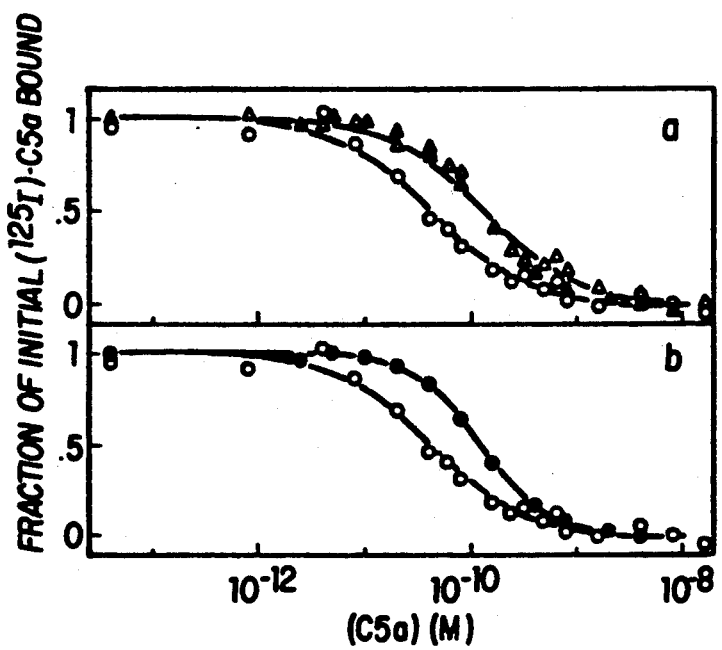
FIG. 2 shows the concentration dependencies of binding in intact membranes and solubilized membranes.

Prior to the isolation, the equilibrium properties of the solubilized receptor, in various states, were determined from competition binding experiments. In these studies receptor was incubated with limiting amounts of $^{125}$I-C5a (20–40 pM) in the presence of increasing concentrations of unlabeled C5a. The results of representative experiments are presented in FIG. 2 which shows concentration dependencies of binding: a, intact membranes (○), β-dodecyl maltoside-solubilized membranes (△), and digitonin-solubilized membranes (▲). b, intact membranes (○) and intact cells (●). These assays were performed by adding increasing amounts of unlabeled C5a to compete against a constant amount of $^{125}$I-C5a. Values for nonspecific binding have been subtracted, and the data have been normalized to facilitate comparison. The total $^{125}$I-C5a added and bound and the nonspecific backgrounds are 9,700, 2,500, and 700 cpm for intact membranes; 9,700, 2,200, and 700 cpm for β-dodecyl maltoside- solubilized membranes; 15,000, 3,500, and 350 cpm for intact cells. All values are the averages of duplicate determinations. The $IC_{50}$ values are 40, 110, and 110 pM for receptor in intact membranes and membranes solubilized in digitonin or β-dodecyl maltoside, respectively (FIG. 2a). The corresponding $K_d$ values, as determined by the program LIGAND (Munson, P. J., and Rodbard, D. (1980) Anal. Biochem. 107, 220-239), are 20±5, 90±15, and 90±12 pM. Analysis with LIGAND revealed only a single class of binding sites in any of the conditions studied. The similarity in the affinities of the membrane-bound and detergent-solubilized receptor for C5a indicates that large conformational changes have not occured in the receptor upon its solubilization from the membrane. It is interesting to note that the $K_d$ of the receptors in detergent is almost identical to the $K_d$ in whole cells.

We have measured the equilibrium binding properties of receptor purified by affinity chromatography. The Kd obtained, 60 pM, is within experimental error of the value obtained in crude, digitonin solubilized membrane. These results demonstrate that the receptor as isolated contains all the components needed for normal binding activity. The procedures used for this experiment are the same as those used with the crude, digitonin solublized receptor above.

Figure 3:
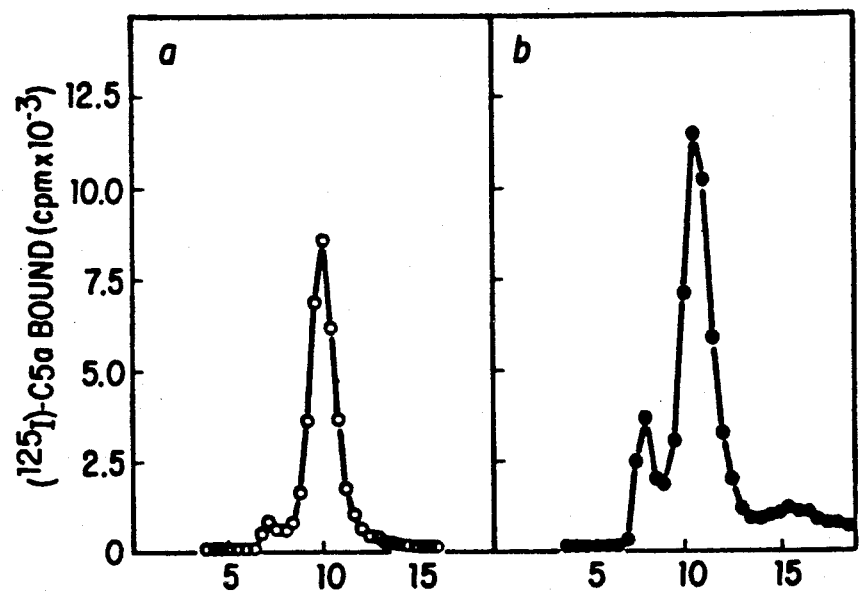
FIG. 3 shows the chromatographic behavior of the solubilized following solubilization in $\beta$dodecyl maltoside.

The chromatographic behavior of the solubilized receptor following solubilization in β-dodecyl maltoside is shown in FIG. 3. In the experiments depicted in FIG. 3, the 160,000 ×g supernatants of β-dodecyl maltoside-solubilized PMN membrane were chromatographed over an HR 10/30 Superose-12 column (Pharmacia) equilibrated with 0.1M HEPES buffer, pH 7.2, containing 0.1% β-dodecyl maltoside. The column was calibrated with ferritin, catalase, bovine γ-globulin, bovine serum albumin, and chymotrypsin which have molecular masses of 410, 232, 158, 68, and 25 kDa, respectively. These proteins, which were dissolved in the same buffer used to solubilize the membranes, eluted at 8.9, 10.5, 11.3, 11.7, and 17.5 ml, respectively. All of the procedures were carried out at 4° C. a, 20 μg of intact membrane was incubated with 5 ng of $^{125}$I-C5a for 60 min. The membranes were washed once by centrifugation to remove unbound C5a and then solubilized with 300 μl of 0.1M HEPES buffer containing β-dodecyl maltoside. The radioactive peaks were abolished when the binding was performed in the presence of a 100-fold excess of unlabeled C5a. b, 50 μg of membrane was solubilized and 1 ng of $^{125}$I-C5a added to the 160,000×g supernatant. After incubation for 30 min, the material was chromatographed as in a.

Figure 4:
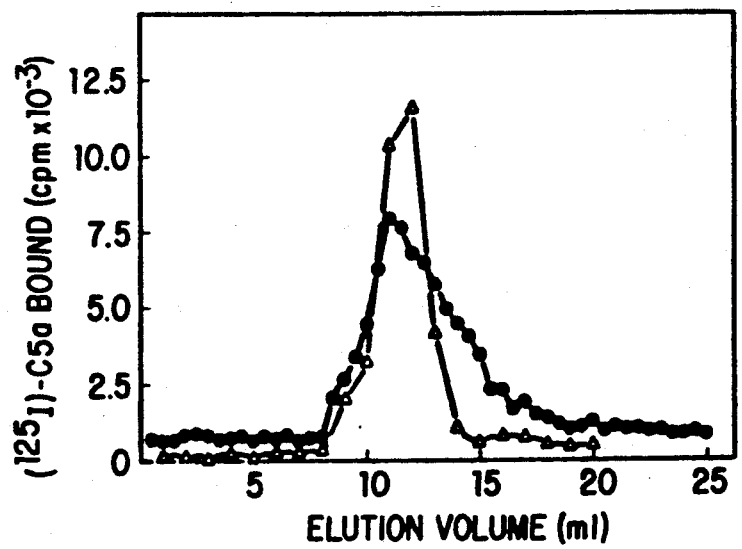
FIG. 4 shows the gel filtration of digitonin-solubilized receptor.

In the initial protocol (FIG. 3a) $^{125}$I-C5a was bound to intact membranes, after which the membranes were solubilized and then chromatographed over a Superose-12 column in a buffer containing 0.1% detergent. The bound C5a was found predominantly in a single peak with a Stokes radius of 52A and an apparent molecular mass of 230 kDa. A small amount of C5a was also observed in elute at the void volume of the column. A second experiment was performed in which the $^{125}$I-C5a was bound to receptor after the membrane was solubilized. The results are essentially identical to those of the first experiment, as the vast majority of the bound C5a eluted with an apparent molecular mass of 230 kDa (FIG. 3b). Again, a small peak was found at the void volume of the column. No free C5a is observed because the column irreversibly adsorbs the unbound ligand. A similar set of results was also obtained with receptor solubilized in digitonin. As illustrated in FIG. 4, digitonin-solubilized receptor to which C5a had been bound (Δ) chromatographed with an apparent molecular mass of 275 kDa.

Gel filtration of digitonin-solubilized receptor. The solubilized receptor was chromatographed according to 2 protocals. In the first (Δ), the solubilized receptor was incubated with $^{125}$I-C5a prior to chromatography, and in the second (●) the receptor was chromatographed without addition of C5a and each fraction tested for its ability to bind C5a as described above.

In the experiments depicted in FIG. 4, the 160,000×g supernatants of digitonin-solubilized PMN membrane were chromatographed over a Superose-12 column equilibrated with 0.1M HEPES buffer, pH 7.2, containing 0.1% digitonin. The column was calibrated with thyroglobulin, ferritin, alcohol dehydrogenase, bovine serum albumin, carbonic anhydrase, and cytochrome c which have masses of 669, 440, 150, 68, 30, and 12.4 kDa, respectively. These proteins, which were dissolved in the same buffer used to solubilize the membranes eluted at 9.0, 10.6, 15.1, 15.8, 18.6, and 24.7 ml, respectively. All procedure were carried out at 4° C.

In the second experiment depicted in FIG. 4 the digitonin solubilized receptor was chromatographed without the prior addition of C5a and the location of the receptor determined by assessing the binding activity of each fraction. The majority of the activity eluted at the same position as did receptor to which C5a had been pre-bound. However, the peak is broad and has a trailing shoulder that is not observed in the prebound experiment. Thus, it appears that the digitonin-solubilized receptor exists in two forms that differ in size: a larger form which constitutes most of the population and has an apparent mass of 275 kDa and a smaller form whose mass is consistent with that of the binding subunit identified in the earlier cross-linking studies (see below). Moreover, the smaller form may be converted to the larger on binding C5a, because it is not present in the experiments in which C5a was bound to the receptor prior to chromatography.

The entity that is actually characterized in these gel filtration experiments is not the receptor itself but rather the complex that exists between the receptor and the solubilizing detergent. In order to calculate the molecular mass of the receptor alone, the contribution of the detergent must be subtracted. While we are not able, at the present time, to perform the sedimentation equilibrium experiments that would allow a rigorous determination of the mass of the bound detergent, a reasonable approximation of this quantity is the mass of the detergent micelle. The masses of the digitonin and β-dodecyl maltoside micelles are 70 and 76 kDa, respectively (Helenius, A., and Simons, K. (1975) Biochim. Biophys. Acta 415, 29-79, Suarez, M. D., Revzin, A., Narlock, R., Kempner, E. S., Thompson, D. A., and Ferguson-Miller, S. (1984) J. Biol. Chem. 259, 13791-13799). Subtraction of these values from the apparent molecular masses of the receptor-detergent complexes gives net apparent masses of 150-200 kDa for the larger form of the receptor. An accurate estimate for the mass of the smaller form is difficult to obtain because it chromatographs as a shoulder on a larger peak. Subtraction of the mass of the digitonin micelle from the estimated mass of this complex gives a mass of 30-70 kDa, a value which is consistent with that of the binding subunit (40-50 kDa).

The Solubilized C5a Receptor Interacts with a GTP-Binding Protein

Figure 5:
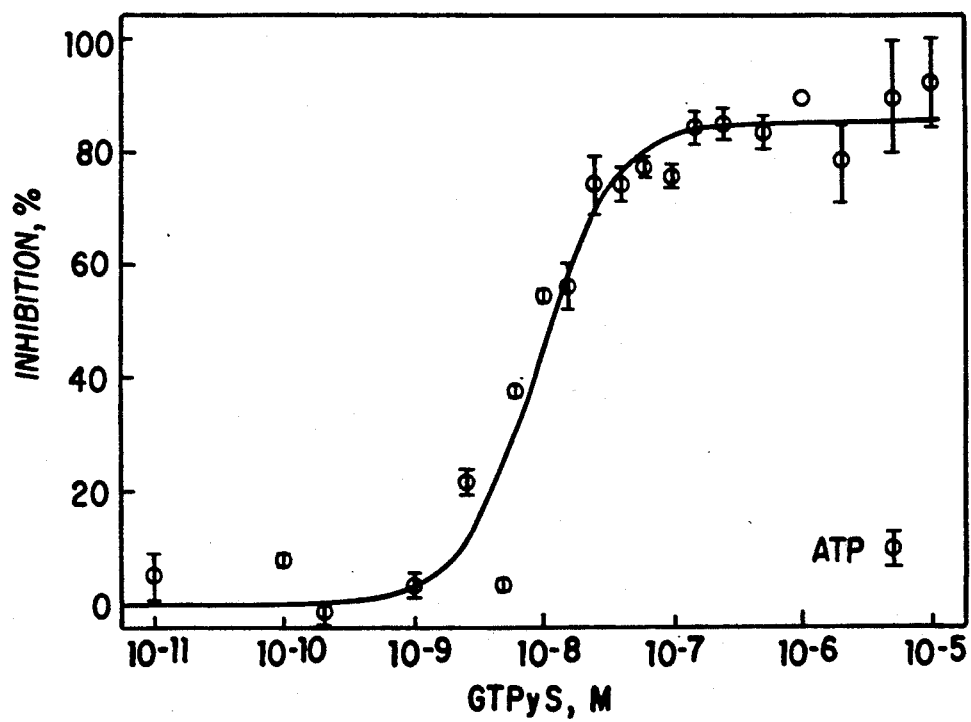
FIG. 5 shows the binding activity of digitonin solubilized membranes in the presence of increasing amounts of GTP$\gamma$S.

The high molecular mass is supported by the results shown in FIG. 5. As shown in FIG. 5 membranes were solubilized in digitonin and assayed for binding activity in the presence of increasing amounts of GTPγS. The interaction between the receptor and its G-protein is preserved in the soluble state. Titration of digitonin solubilized membranes with GTPγS results in a maximum inhibition of C5a binding of 85% with an $IC_{50}$ of 10 nM. These results imply that either; a) the solubilized receptor exists as a physical complex with its G-protein or b) the complex forms in the detergent upon the binding of C5a.

Figure 6B:
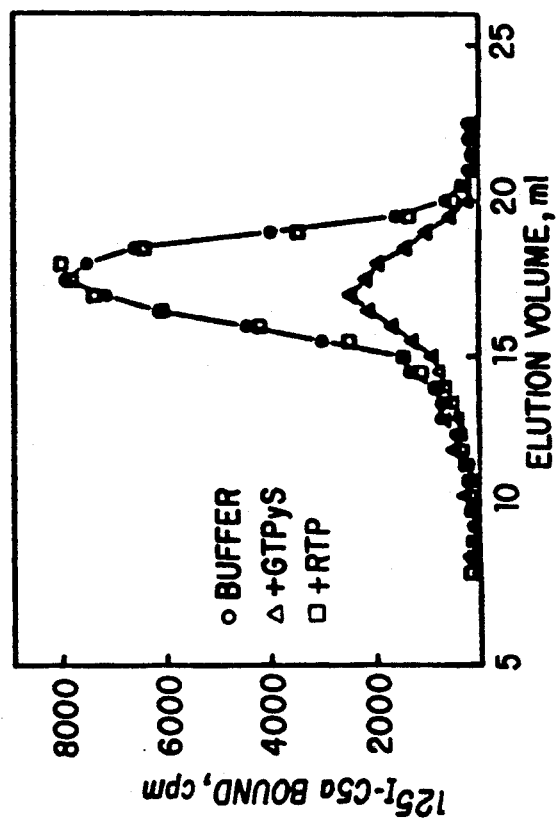
FIG. 6A and FIG. 6B show gel-filtration chromatographs of C5a receptor.
Figure 6A:
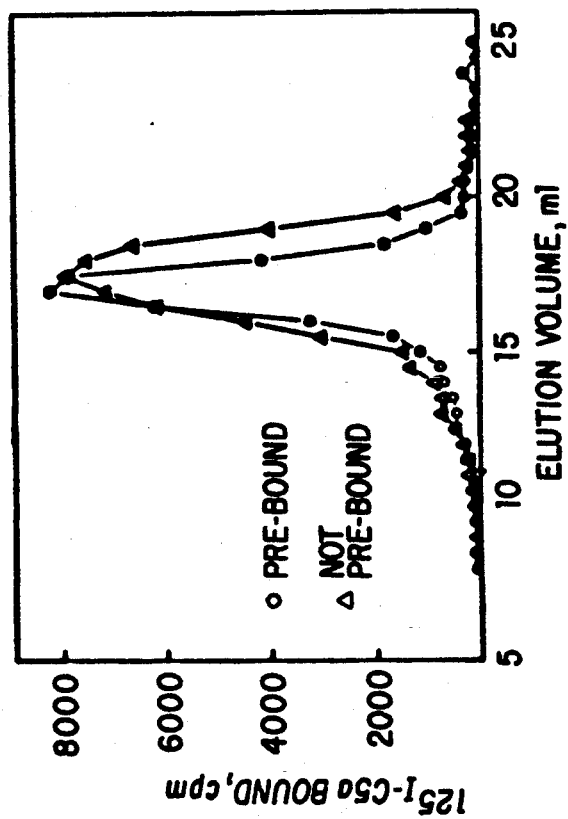

This interaction was studied further by performing gel-filtration chromatography of the C5a receptor using a TSK 4000 column run in 50 mM Tris-Cl, pH 7.2, containing 0.1% digitonin and 5 mM $MgCl_2$. See FIG. 6 In the first protocol $^{125}$I-C5a was bound to the receptor prior to chromatography. The bound C5a was found predominantely in a single peak which eluted with an apparent Mr of 300 kDa (FIG. 6a). The second experiment was performed by chromatographing the solubilized receptor without pre-binding C5a, and then assaying the fractions for binding activity (FIG. 6B). Again the receptor eluted with an apparent molecular mass of 300 kDa. In FIG. 6B the experiment was performed by preincubating solubilized receptor with GTPγS, ATP or buffer followed by chromotography and assaying the fractions for binding activity. The results indicate an effect on C5a binding that is GTPγS specific. While these data suggest that the solubilized receptor is oligomeric, as indicated above, estimates of the molecular weight of membrane proteins from gel-filtration experiments are prone to substantial uncertainties. However, cross-linking experiments with the solubilized receptor support the hypothesis that the receptor is oligomeric.

Cross-linking C5a to the Soluble Receptor—To investigate the structure of the soluble receptor further, we cross-linked $^{125}$I-C5a to the 160,000×g supernatant of β-dodecyl maltoside-solubilized PMN membranes. See FIG. 7.

Figure 7:
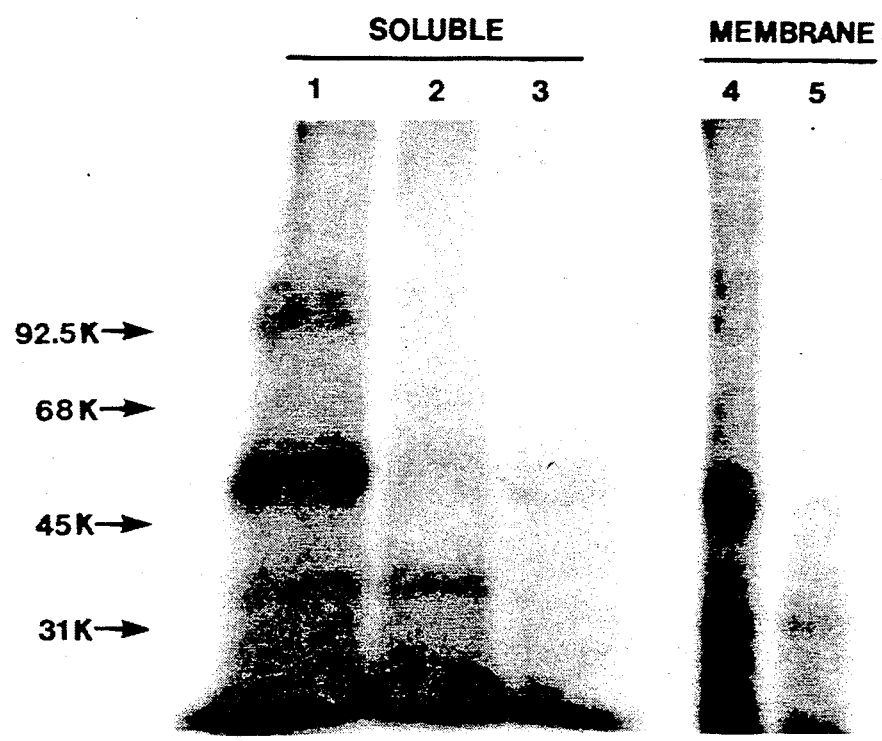

The detergent extract was incubated for 15 min with $^{125}$I-C5a followed by the addition of the cross-linking agent ethylene glycolbis-(succinimidylsuccinate) (EGS). The reaction was quenched after 30 min with Tris-Cl. The 160,000×g supernatant from 125 μg of PMN membrane solubilized with 1% β-dodecyl maltoside or 30 μg of intact membrane was incubated with the indicated reagents at 4° C. Cross-linking, SDS PAGE, and autoradiography were performed as described in the procedures section. Lanes 1-3 are with the soluble receptor and lanes 4-5 with the membrane-bound receptor. Lanes 1 and 4, $^{125}$I-C5a+EGS; lanes 2 and 5, $^{125}$I-C5a+EGS+100-fold excess of unlabeled C5a; lane 3, $^{125}$I-C5a without EGS. Autoradiography revealed three bands with molecular masses of 35, 52, and 95 kDa (FIG. 7, lane 1). The two larger bands represent specific complexes between C5a and proteins in the extract, because they largely disappear when the experiment is repeated in the presence of an excess of unlabeled C5a (FIG. 7, lane 2). The 35-kDa moiety appears to result from a nonspecific interaction, because it is unaffected by the excess of unlabeled C5a. While the majority of the specifically cross-linked C5a is found at the expected position (molecular mass=52 kDa), a substantial fraction (>20%) is present in the 95-kDa species, a finding which is consistent with the gel filtration studies and which implies that the receptor, as solubilized, consists of more than a single polypeptide chain. Because the results of these cross-linking experiments differ from those reported for intact PMN or PMN membranes (20-22), we repeated the experiments using non-solubilized membranes (FIG. 7, lanes 4, 5). As reported previously, the vast majority of the specifically cross-linked C5a is found in the 52-kDa species with only trace amounts present in the larger molecule.

Figure 8:
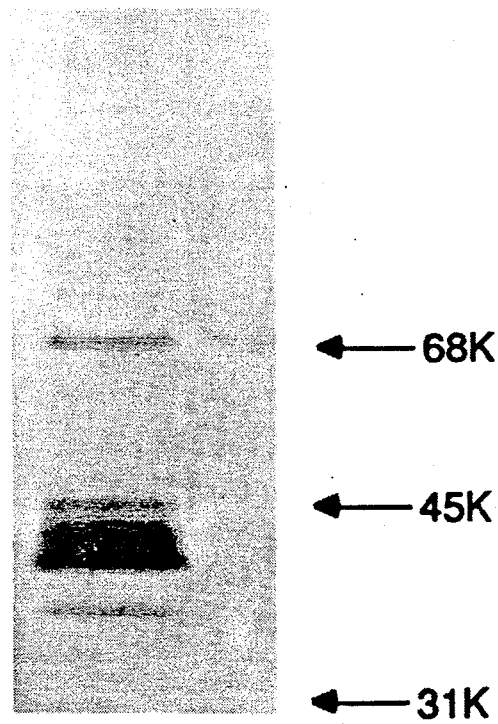
FIG. 8 is an SDS-Page of a fraction containing solubilized C5a receptor purified by C5a affinity chromatography followed by gel-filtration and ion-exchange chromatography.

The C5a solubilized receptor was purified by C5a affinity chromatography followed by gel-filtration and ion-exchange chromatography. The resultant silver-stained SDS-PAGE pattern is shown in FIG. 8.

Four bands are present (the additional bands at 68 and 75 kDa are contaminants which were inadvertently added prior to electrophoresis) with Mr's of 35, 41, 42-44 and 45 kDa. This same constellation of bands, in the same relative proportions, was found after each of the 3 steps in the purification. Furthermore analysis across the peaks of activity in both the gel-filtration and ion-exchange steps showed no separation of the different bands. Binding of C5a to the purified receptor is sensitive to inhibition by GTPγS (27-50% in 3 different preparations), but not to ATP. This strongly suggests that the "receptor" as solubilized is a complex between the C5a binding subunit and one or more G-proteins. In this regard the Mr's of the alpha subunits of Gi and Gs are 40-41 and 45 kDa, respectively, and that for the beta subunit is 35 kDa.

We had previously concluded from these data that the solubilized receptor is a physical complex of all four polypeptides. As indicated below we now know the 45 kDa polypeptide is not part of the receptor.

A procedure in which C5a is bound to receptor prior to affinity chromatography provides significant additional evidence that the C5a receptor is composed of the 35, 40 and 42-44 kDa polypeptides. This experiment also demonstrates that the 45 kDa polypeptide, previously thought to be part of the receptor, binds to the affinity column non-specifically and is not related to the receptor.

Figure 9:
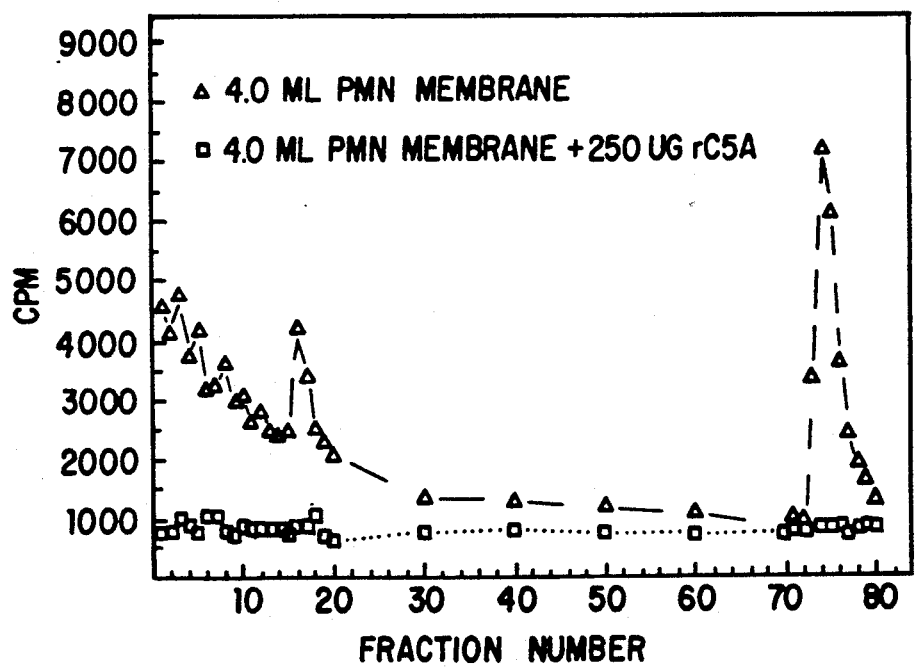
FIG. 9 shows the activity of eluted solubilized C5a receptor as a function of fraction number.

Human PMN membrane was solubilized in digitonin as described above. One aliquot was incubated for 30 min a 0° C. with buffer and a second aliquot was similarly incubated with C5a at a concentration of 3 uM. Each sample was then chromatographed over the C5a affinity column as described previously. As shown in FIG. 9 a peak of C5a binding activity was eluted from the sample incubated with buffer, but no binding activity was eluted from the C5a incubated sample.

Figure 10:
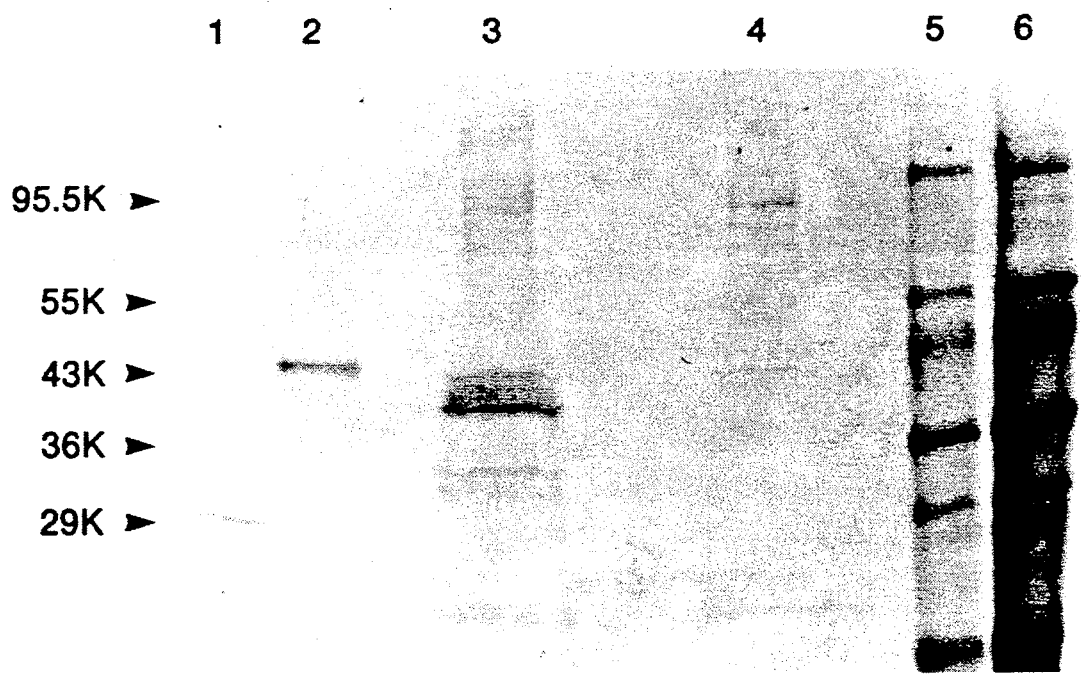
FIG. 10 is an SDS-page of material prepared by C5a affinity chromatography. The receptor is shown to consist of polypeptide with molecular mass of 35, 40 and 42 kDa. The 45 kDa band is shown to be non-specific.

The fractions containing the C5a binding activity (73-76) from the untreated sample, and the same set of fractions from the C5a treated sample were pooled separately, concentrated, and then subjected to SDS PAGE (FIG. 10). The untreated sample (lane 3) contains the expected constellation of bands at 35, 40, 42-44 and 45 kDa. The C5a treated sample (lane 4) lacks the bands at 35, 40 and 42-44 kDa indicating that these polypeptides bind specifically to the column and comprise the receptor. However, the 45 kDa band is unaffected by the pre-incubation with C5a (compare lanes 3 and 4) demonstrating that this polypeptide binds to the column non-specifically and is not part of the receptor.

With this protocol if digitonin solubilized membrane is incubated with a saturating concentration of C5a prior to affinity chromatography the C5a receptor will not bind to the column, but instead will flow through. Thus, any protein isolated from the column under these conditions must adhere non-specifically and cannot be part of the receptor. When this experiment was carried out the 35, 40 and 42-44 KDa polypeptides disappeared, providing further evidence that they comprise the receptor. On the other hand the band at 45 KDa was still observed indicating that it bound to the column non-specifically and is not part of the receptor.

USE OF THE PURIFIED C5a RECEPTOR

As described above, purified C5a can be used in a wide variety of manners which take advantage of its specific affinity for binding agents having C5a activity. The following example is illustrative thereof.

The purified receptor can be used to screen for C5a antagonists by assessing a compounds ability to inhibit the binding of C5a to the receptor. The assays are carried out by adding assay buffer (50 mM HEPES, pH 7.2 containing 5 mM $MgCl_2$, 1 mM $CaCl_2$, 0.5% BSA and 0.1% digitonin), the compound to be tested or solvent, and $^{125}$I-C5a to a final volume of 200 µl and incubating the mixture for 15-30 min at temperatures of 4-20 C. At this time 1 ml of 50 mM HEPES, pH 7.2, containing 9.6% PEG, 0.1% BSA, 5 mM $MgCl_2$, and 1 mM $CaCl_2$ is added and the sample mixed vigorously. After an additional 5 min the sample is filtered through a polyethyleneimine treated GF/C filter and the filter washed with 2 ml of the same buffer. Non-specific backgrounds are determined by including a 100-fold excess of unlabelled C5a in the binding assay. The inhibitory activity of a compound is assessed by comparing the binding of C5a in the presence of the compound with the binding in its absence (the solvent control). The use of purified receptor instead of intact membranes containing the receptor is advantagious because the system is a soluble one, and does not contain all of the other components which comprise membranes. For these reasons assays which use purified receptor are less prone to non-specific interference (e.g. by a membrane active compound), and are less likely to generate false positives.

EXAMPLE 2

Process and product as described in Example 1 except that C5a receptor is isolated from macrophage, eosinophil, ATCC U937, or HL60 cell preparations rather than leukocyte concentrate.

EXAMPLE 3

Process and product as described in Examples 1 except that C5a is obtained from plasma by the procedure described above rather than expressed in a recombinant organism.

EXAMPLE 4

Process and product as described in Examples 1 or 2 except that β-dodecyl maltoside is substituted for digitonin.

EXAMPLE 5

Process and product as described in Examples 1, 2 or 3 except that the membrane is treated with detergent at 24° C. rather than 4° C.

What is claimed is:

1. A C5a receptor, the receptor having a $K_d$ of binding C5a approximately equal to that of C5a receptor on intact cells, having a molecular mass of 42 kDa when determined by SDS-PAGE under reducing conditions; and containing less than 10% other cellular matter and plasma with the proviso that the preparation need not be free of one or more associated G-proteins.

2. A C5a receptor according to claim 1 wherein the C5a receptor concentration is at least 100,000-fold purified relative to C5a receptor found on human polymorphonuclear leukocytes.

3. A highly purified and concentrated C5a receptor having the activity of binding C5a, said C5a receptor prepared by the steps comprising:
   (a) solubilizing an impure preparation selected from the group consisting of polymorphonuclear leukocytes, macrophage, eosinophil, ATCC U937 and HL60, said solubilizing comprising, addition of a solution buffered at pH 6 to 8 with 50 mM N-2-hydroxyethylpiperazine-N'-2-ethanesulfonic acid, said solution containing approximately 0.5 to 2.0% of a first detergent which is digitonin, to the impure preparation;
   (b) contacting the impure preparation with a matrix to which an agent specfic for C5a binding activity has been bound;
   (c) adsorbing from the impure preparation, C5a receptor having C5a binding activity onto said matrix;
   (d) removing the impurities from the C5a receptor bound to said agent; and
   (e) desorbing the C5a receptor from said matrix, said desorbing step comprising, eluting the C5a receptor with a solution buffered at pH 4.0 to 5.0, said solution containing 0.05% to 0.5% of a second detergent which is digitonin, to the impure preparation; and 0.1 to 0.4M of a chaotrope.

4. A C5a receptor of claim 3 wherein said C5a receptor is isolated from polymorphonuclear leukocytes from human plasma and is associated with one or more G-proteins and contains less than 10% other cellular matter and plasma.

5. A C5a receptor preparation according to claim 3, the preparation having a $K_d$ of binding C5a approximately equal to that of C5a receptor on intact cells, having a molecular mass of 42 kDa when determined by SDS-PAGE, under reducing conditions; and containing less than 10% other cellular matter and plasma with the proviso that the preparation need not be free of one or more associated G-proteins.

6. A C5a receptor of claim 5 wherein the C5a receptor is at least 100,000-fold purified relative to C5a receptor found on human polymorphonuclear leukocytes.

* * * * *